United States Patent
Rubin

(10) Patent No.: US 8,758,379 B2
(45) Date of Patent: *Jun. 24, 2014

(54) ROTARY CUTTING TOOL WITH IMPROVED CUTTING AND REDUCED CLOGGING ON SOFT TISSUE AND THIN BONE

(71) Applicant: Medtronic-Xomed, Inc., Jacksonville, FL (US)

(72) Inventor: Joshua David Rubin, McLean, VA (US)

(73) Assignee: Medtronic-Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/801,147

(22) Filed: Mar. 13, 2013

(65) Prior Publication Data
US 2013/0197522 A1 Aug. 1, 2013

Related U.S. Application Data

(63) Continuation of application No. 12/771,537, filed on Apr. 30, 2010, now Pat. No. 8,409,235.

(51) Int. Cl.
*A61B 17/32* (2006.01)

(52) U.S. Cl.
USPC .......................................................... 606/180

(58) Field of Classification Search
USPC .................... 606/167, 169–171, 180; 604/22; 600/565–568
See application file for complete search history.

(56) References Cited

U.S. PATENT DOCUMENTS

| | | |
|---|---|---|
| 5,286,253 A | 2/1994 | Fucci |
| 5,411,514 A | 5/1995 | Fucci et al. |
| 5,591,187 A | 1/1997 | Dekel |
| 5,592,727 A | 1/1997 | Glowa et al. |
| 5,601,583 A | 2/1997 | Donahue et al. |
| 5,620,447 A | 4/1997 | Smith et al. |
| 5,669,921 A | 9/1997 | Berman et al. |
| 5,769,086 A | 6/1998 | Ritchart et al. |
| 5,910,133 A | 6/1999 | Gould |
| 5,916,231 A | 6/1999 | Bays |
| 6,214,009 B1 | 4/2001 | Toriumi et al. |
| 6,375,635 B1 | 4/2002 | Moutafis et al. |
| 2003/0163126 A1 | 8/2003 | West, Jr. |
| 2003/0181934 A1 | 9/2003 | Johnston et al. |
| 2005/0277970 A1 | 12/2005 | Norman et al. |
| 2006/0200123 A1 | 9/2006 | Ryan |

FOREIGN PATENT DOCUMENTS

GB 2 379 878 A 3/2003

*Primary Examiner* — Ryan Severson
(74) *Attorney, Agent, or Firm* — Dicke, Billig & Czaja, PLLC

(57) ABSTRACT

A surgical cutting instrument including two coaxially arranged tubular members. The first tubular member has a cutting tip and is co-axially disposed within the second tubular member, which in turn has a cutting window to expose the cutting tip to tissue and bone through the cutting window. Movement of the tubular members with respect to each other debrides soft tissue and thin bone presented to the cutting window. The second (outer) tubular member has one or more features which contribute to reduced clogging of the cutting tip as a whole.

6 Claims, 4 Drawing Sheets

ROTARY CUTTING TOOL WITH IMPROVED CUTTING AND REDUCED CLOGGING ON SOFT TISSUE AND THIN BONE

CROSS-REFERENCE TO RELATED APPLICATION

This application is a continuation of U.S. patent application Ser. No. 12/771,537, filed Apr. 30, 2010, entitled "Rotary Cutting Tool with Improved Cutting and Reduced Clogging on Soft Tissue and Thin Bone," now U.S. Pat. No. 8,409,235, issued Apr. 2, 2013, the entire contents of which are incorporated by reference here.

BACKGROUND

Surgical cutting instruments in which an elongated inner member (i.e., solid shaft or tube) is rotated within an elongated outer tubular member have become well accepted in surgical procedures where access to the surgical site is gained via a narrow portal or passage. Typically, the outer tubular member includes a distal end forming an opening defining a cutting window or port, and the inner member includes a distal end forming a cutting tip for cutting bodily tissue at the window. Proximal ends of the inner and outer members are commonly secured to hubs that, in turn, are attached to a powered handpiece for rotating and/or oscillating the inner member relative to the outer tubular member. The cutting tip of the inner member can have various configurations specific to the surgical procedure in question (e.g., cutting, resecting, abrading, shaving, etc.), with the cutting window being suitably configured to cooperate with a particular configuration of the cutting tip.

Often, the inner member is not solid but tubular so that the loose tissue resulting from a cutting, resecting, or abrading procedure can be aspirated through the hollow lumen of the inner member. With specific reference to ENT (i.e., ear, nose, and throat) applications, such as sinus surgery, adenoidectomy, laryngeal surgery, etc., extremely sharp, micro-resecting blades or cutting tips are typically employed to effectuate the desired procedure.

Use of such surgical cutting instruments generally entails delivering the cutting window/cutting tip to the target site and positioning the cutting window such that the cutting tip is "exposed" to the desired tissue. Once the desired tissue has been treated, other tissue may be addressed, by positioning the cutting window to expose the cutting tip to such other tissue. A variety of types of tissue may be the subject of a given surgical procedure. Thus, while upon initial placement at the target site the cutting window may be the optimum design for a first portion of the procedure, tissue at a different location will also require removal, and such tissue may or may not be the same type as previously encountered. If not, the instrument may no longer be the optimum design for the type of tissue newly presented to the instrument.

In addition, and regardless of tissue type, obstruction of the surgical cutting instrument clearly is a problem. In particular, some types of tissue (e.g., thin bone) are prone to cause such surgical instruments to clog more often than other types of tissue, or (perhaps more importantly) more often than the surgeon desires (i.e., never). Such clogging generally may require removal of the cutting window/cutting tip from the target site, and either cleaning out the window or replacing some or all of the apparatus entirely. This extends the surgical procedure, which is undesirable.

If the surgical cutting instrument is used with an image guided surgery (IGS) system, additional concerns may arise. In particular, IGS generally entails registering the cutting window/cutting tip once deployed to the target site. Following reinsertion of the cutting instrument, the cutting window/cutting tip must be re-registered relative to the IGS system, further extending the surgical procedure.

Compounding the clogging problem is the reality that different types of tissue have different propensities to clog a given apparatus. It is generally undesirable to require a surgeon to use as many configurations of cutting tip/cutting window as there are types of tissue encountered in a given procedure. Similarly, it is generally undesirable to require a surgeon to use as many configurations of cutting tip/cutting window as there are types of procedures likely to be encountered within the realm of ENT surgery (note the wide variety of procedures listed above).

Thus, while surgical cutting instruments continue to be extremely useful, the need to prohibit clogging of the cutting window has not been fully addressed, particularly when considering the wide variety of tissue types and procedures involved. Therefore, a surgical cutting instrument designed to reduce clogging, despite being exposed to a variety of tissue types and/or a variety of procedures, is very much needed.

SUMMARY

In general terms, a surgical cutting instrument includes two coaxially arranged tubular members. The first tubular member has a cutting tip and is co-axially disposed within the second tubular member, which in turn has a cutting window to expose the cutting tip to tissue and bone through the cutting window. Movement of the tubular members with respect to each other debrides soft tissue and thin bone presented to the cutting window. The second (outer) tubular member has one or more features which contribute to reduced clogging of the cutting tip as a whole.

In one embodiment, a surgical cutting instrument includes two coaxially arranged tubular members. The first tubular member has a cutting tip and is co-axially disposed within the second tubular member, which in turn has a cutting window to expose the cutting tip to tissue and bone through the cutting window. Movement of the tubular members with respect to each other (such as rotation of one or both about the central axis, or longitudinally along such axis) debrides soft tissue and thin bone presented to the cutting window. The second (outer) tubular member has a pair of cutting teeth which contribute to the cutting action. The geometry of the teeth contributes to reduced clogging of the cutting tip as a whole, specifically, the cutting window comprises first and second open sections separated from each other by the pair of oppositely facing teeth. The area occupied by the teeth, in what would otherwise be the open cutting window, contributes to reduced clogging of the cutting window by reducing the size of tissue particles (particularly pieces of soft bone) that may enter (and thus become stuck in) the cutting window.

In another embodiment, a surgical cutting instrument includes two coaxially arranged tubular members. The first tubular member has a cutting tip and is co-axially disposed within the second tubular member, which in turn has a cutting window to expose the cutting tip to tissue and bone through the cutting window. Movement of the tubular members with respect to each other (such as rotation of one or both about the central axis, or longitudinally along such axis) debrides soft tissue and thin bone presented to the cutting window. It is not necessary to require the second, outer tubular member to have a pair of teeth; instead, the cutting window may be described simply as comprising first and second open sections, the first open section of the cutting window having an area denoted A, and the hollow first member having a cross-sectional area denoted B, A and B being in a ratio between about 1:1 and 2:1.

In another embodiment, a surgical cutting instrument includes two coaxially arranged tubular members. The first tubular member has a cutting tip and is co-axially disposed within the second tubular member, which in turn has a cutting window to expose the cutting tip to tissue and bone through the cutting window. Movement of the tubular members with respect to each other (such as rotation of one or both about the central axis, or longitudinally along such axis) debrides soft tissue and thin bone presented to the cutting window. Independent of dimensions, the cutting window comprises a proximal, trapezoidal "base" portion and a generally semicircular distal portion.

Other embodiments and variations are possible beyond those described in this Summary section, and therefore nothing in this Summary section should be taken as expressing a requirement applicable to any particular commercial embodiment.

DETAILED DESCRIPTION

Figure 1:
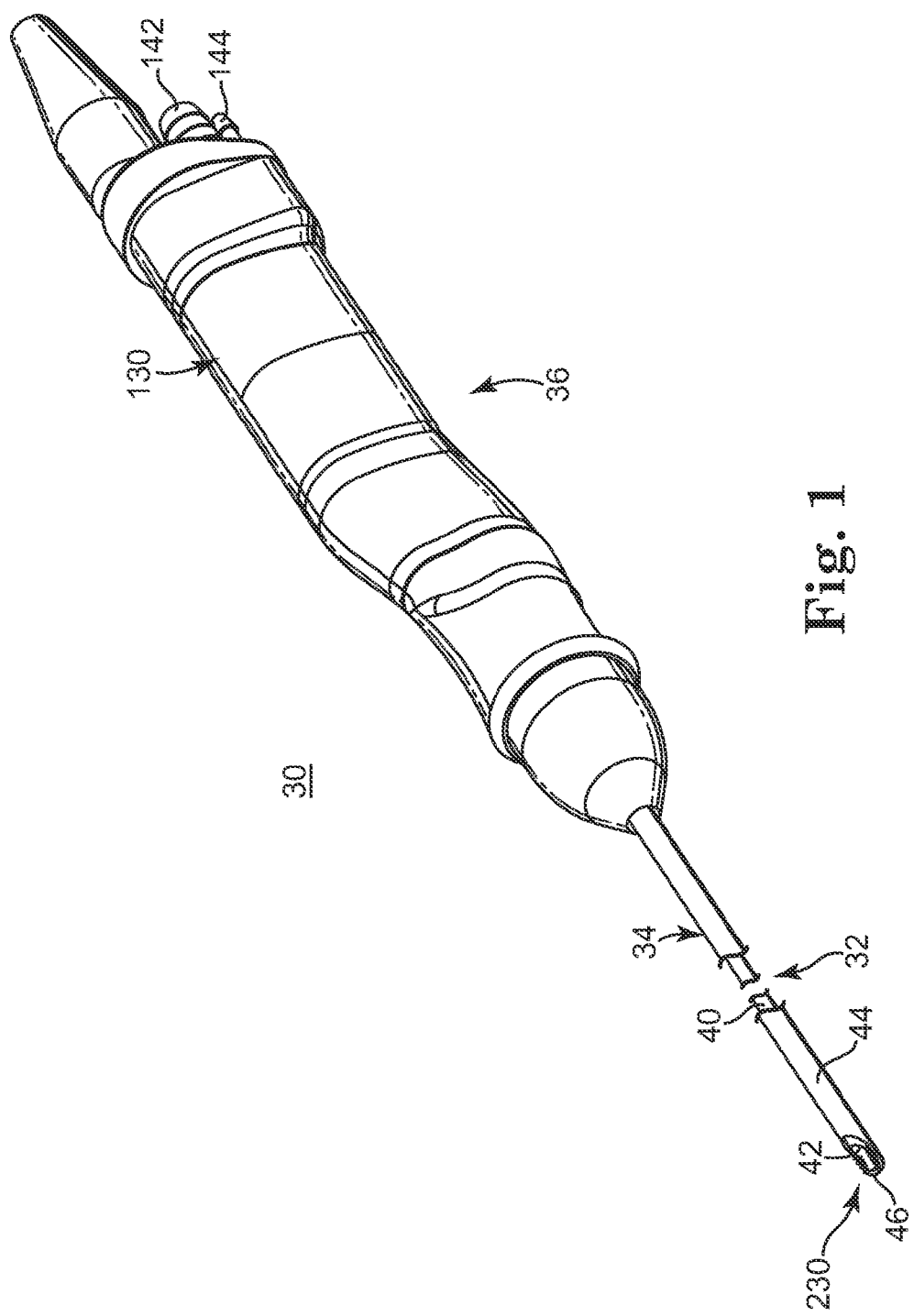
FIG. 1 is a perspective view of one embodiment of a surgical cutting instrument.

An earlier version of a surgical cutting instrument generally similar to that described below may be found in United States Patent Application Publication No. US 2005/0277970, which is incorporated by reference. In general terms, such instruments include a proximal handpiece and a tool extending distally from the handpiece. In this vein, one preferred embodiment of an improved surgical cutting instrument 30 is illustrated in FIG. 1. The surgical cutting instrument 30 includes a first blade member or assembly 32, a second blade member or assembly 34, a handpiece 36. The components are conventional or described in greater detail below. In general terms, however, the first blade assembly 32 includes a first tubular member 40 which has a cutting tip 42. The second blade assembly 34 includes a second tubular member 44 which has a cutting window 46. The first tubular member 40 is co-axially disposed within the second tubular member 44 such that the cutting tip 42 is exposed at the cutting window 46 at the distal end 230 of cutting instrument 30.

Figure 2:
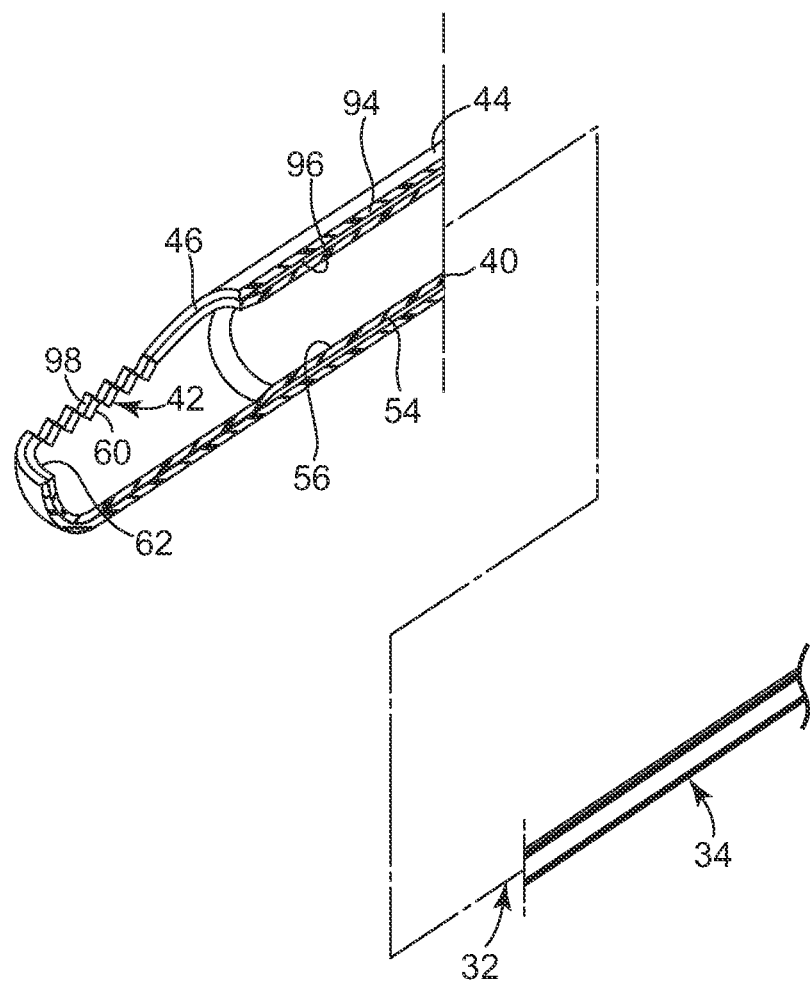
FIG. 2 is a partial cross-sectional schematic view of the distal portion of the instrument of FIG. 1, enlarged for clarity.

The general construction of the distal end 230 is shown in greater detail in FIG. 2, although FIG. 2 should not be used to limit the configuration of actual cutting surfaces, as it shows such features only in schematic form. (For the details of the cutting surfaces, see FIGS. 3A and 3B, discussed below.) Distal end 230 comprises the distal potions of the first tubular member 40, which includes a central lumen 56 extending to a distal section 54. The distal section 54 forms the cutting tip 42 that is optimally configured to perform a desired cutting procedure. The cutting tip 42 comprises a serrated edge 60 surrounding a distal opening 62 of the lumen 56. The first tubular member 40 may be a rigid material, such as 304 stainless steel, and linear in longitudinal extension. Alternatively, the first tubular member 40 can be configured to be bendable instead of linear, according to known principles not specifically illustrated here. The second tubular member 44 has a proximal region 92, a distal region 94, and a lumen 96 connecting the two regions. The distal region 94 integrally forms the cutting window 46 that is otherwise fluidly connected to the lumen 96. The cutting window 46 comprises a serrated edge 98. The pair of tubular members may be rigid and longitudinally straight or linear. In alternative embodiments, not specifically illustrated here, the tubular members can incorporate, or be forced to assume, one or more bends.

Regardless of whether straight or bent (or bendable), the second tubular member 44, and in particular the lumen 96, is sized to co-axially receive the first tubular member 40 in a manner that allows rotation and/or oscillation of the first tubular member 40 relative to second tubular member 44 while providing a path for internal irrigation. Thus, the lumen 96 of the second tubular member 44 preferably has a diameter slightly greater than an outer diameter of a corresponding portion of the first tubular member 40, to define an irrigation path.

Also, the housing 130 can define an internal aspiration path and a separate internal irrigation path (each not shown). The aspiration path is fluidly connected (directly or indirectly) to the first tubular member 40 (FIG. 2) for aspirating material from the cutting tip 42. In this regard, and in one embodiment, the handpiece 36 further includes an aspiration port assembled to the housing 130 in fluid communication with the aspiration path. Alternatively, the aspiration port 142 can be integrally formed by the housing 130. Regardless, the aspiration port 142 is adapted for connection to tubing (not shown) that in turn is connected to a vacuum source (not shown) for applying a vacuum to the aspiration path, and thus (directly or indirectly) to the first tubular member 40. Similarly, the irrigation path is formed within the housing 130, extending from an irrigation port 144. The irrigation port 144, in turn, is adapted for fluid connection to tubing (not shown) that is otherwise connected to a fluid source (not shown). Thus, the handpiece 36 provides for internal irrigation. In one embodiment, the irrigation path is defined by a tube extending within the housing 130. Alternatively, the housing 130 can form a bore that defines the irrigation path without a separate tube. Alternatively, the surgical cutting instrument can be adapted to employ external irrigation using known techniques.

As known in the art, the handpiece 36 can support a motor, and various couplings as required, within its housing 130, although the motor could be remotely located and coupled to the apparatus as appropriate. If the motor is within the housing 130, it typically includes a drive shaft rotatably driven by the motor and connected through various couplings to other portions of the apparatus as required. The motor may be an electrical motor or other alternative design (e.g., pneumatic).

As noted before, the cutting tip 42 provided by the first tubular member 40 is selectively exposed to tissue through the cutting window 46. For example, if the two components are movable relative to one another, such rotation will selectively expose the cutting tip 42 to tissue through the cutting window 46. Upon motion (e.g., rotation) of the first tubular member 40 relative to the second tubular member 44, or vice-versa, the respective serrated edges of the cutting tip 42 and the cutting window 46 combine to perform surgical cutting.

Specific surgical techniques facilitated by the surgical cutting instruments are described below. In general terms, however, during use, a user (not shown) grasps the handpiece 36, and in particular the housing 130, manipulating the handpiece 36 to deploy the distal end 230 to a target site. The surgical cutting instrument 30 can then be operated to remove one or more types of tissue from each of one or more target sites. For example, the surgical procedure in question may require removal of any of the various types of soft tissue or thin bone from the target site.

As illustrated in FIGS. 3A-3B and 4A-4B, cutting window 46 is a multi-sectional opening comprising at least a proximal first opening 46a and a distal second opening 46b, which two openings are joined to each other. They are joined between the points of two medially directed and oppositely pointed teeth 47a, 47b (i.e., each tooth is pointed toward the center and thus toward the other tooth). The teeth are formed by the geometry of the first and second openings 46a, 46b.

Figure 3A:
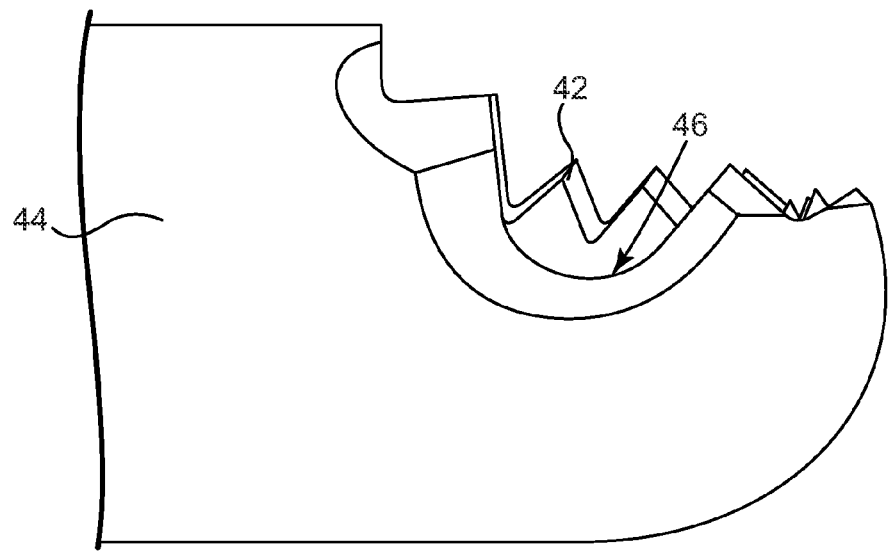
FIGS. 3A and 3B are side and top views, respectively, of an embodiment of a distal portion of a surgical cutting instrument.
Figure 3B:
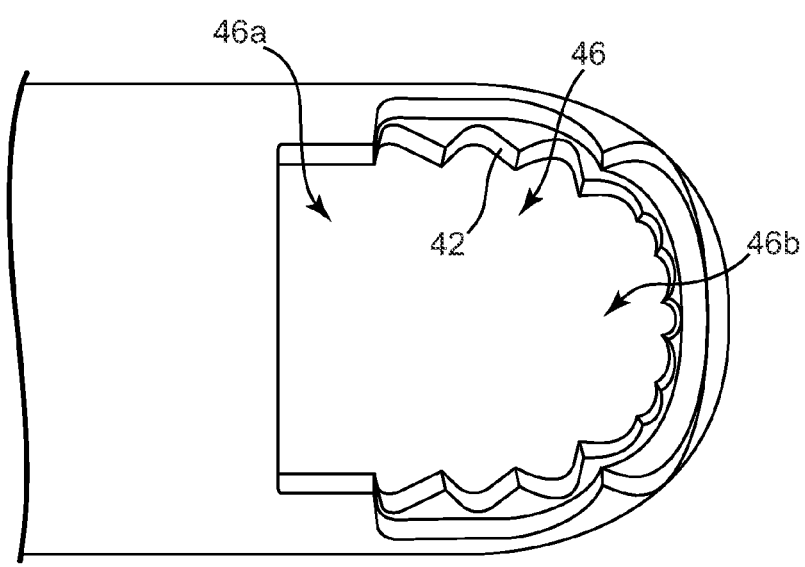
Figure 4A:
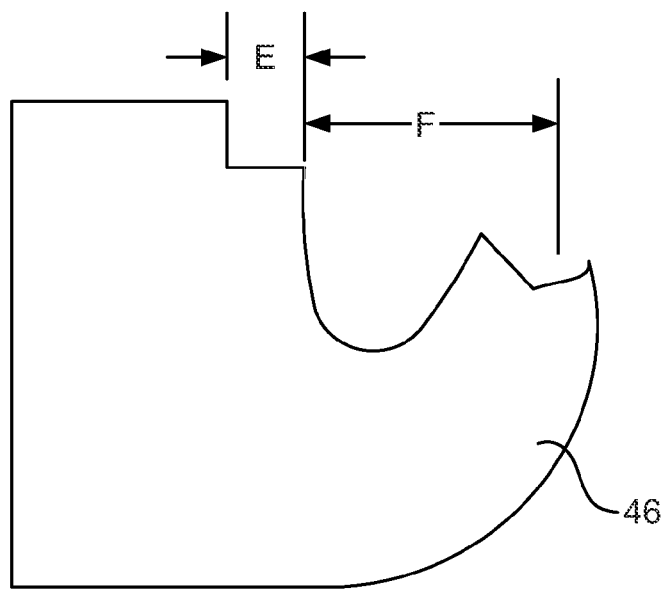
FIGS. 4A and 4B are side and top schematic views, respectively, generally corresponding to the respective views of FIGS. 3A-3B but simplified by omitting structural details and thus not necessarily the actual structure illustrated in FIGS. 3A and 3B.
Figure 4B:
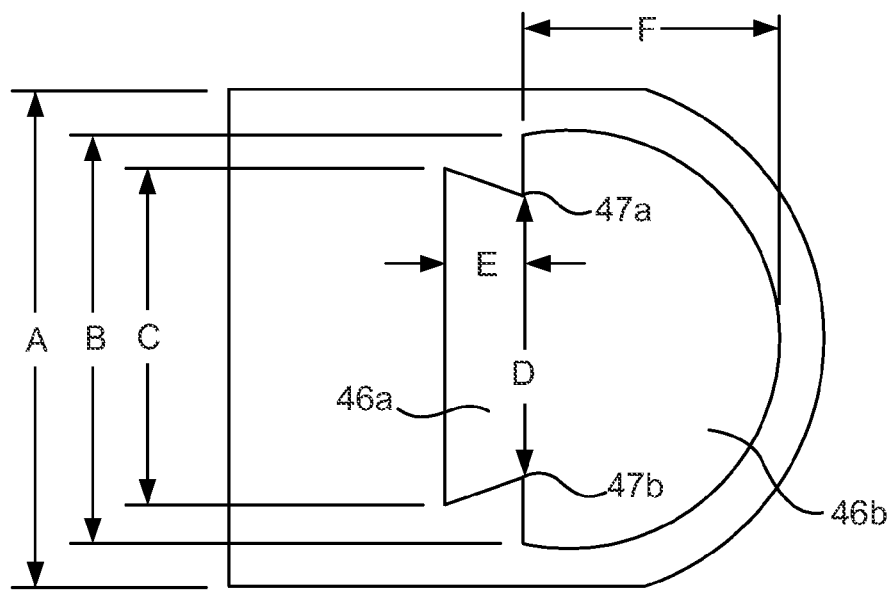

FIGS. 4A and 4B correspond to respective FIGS. 3A and 3B but omit details for clarity only and are thus designed only to show geometrical relationships and not necessarily actual structure. However, reading the figures together, it may be seen from the two top views (FIGS. 3B and 4B) that a preferred embodiment of the cutting window comprises a proximal, trapezoidal "base" portion and a generally semicircular distal portion.

In particular, proximal opening 46a has a transverse width C (see particularly FIG. 4B) which is greater than the distance between the teeth D, measured at the junction of the proximal and distal openings 46a and 46b, respectively. Similarly, the distal opening 46b has a transverse width B which is greater than the distance between the teeth D. In general, there is no direct relationship between C and B but it is preferred that the relationship D<C<B be true as this increases the volume of the distal second opening 46b and that opening is a major contributor to the overall capacity of the instrument to remove soft tissue and thin bone.

Returning to the distal portion 46b, it is generally semicircular as depicted here for the preferred embodiment that is illustrated by way of example only. In general, the distal opening has width D as described above and length F as illustrated in FIG. 4B. The generally semicircular preferred embodiment implies that the value of F is approximately twice the value of D, but in general the distal opening may be elongated as desired for a given diameter of cutting instrument (which, along with the thicknesses of materials chosen, manufacturing tolerances and clearances, and similar factors, allows one to determine the approximately value of D).

Although the first and second tubular members work with each other to accomplish surgical cutting, it very general terms it may be said that the area of the proximal region 46a of the second tubular member is generally correlated with increased ability to resist clogging by soft tissue and bone. Thus, in addition to its transverse measurements C and D, it has a longitudinal length E (corresponding to the height of the trapezoid in that preferred embodiment) and thus the parameters C-E may be used to determine the area of the proximal region 46a according to known equations. Similarly, the area of the distal region 46b may be calculated according to known equations. Alternatively, given a sample of a commercial embodiment, the area(s) may be determined by conventional techniques.

Of course, it should be remembered that the parameters A through E denote endpoints of measurements and thus the measurements themselves may be made directly between such points along straight lines, or along the edges and surfaces of the cutting tip that lie between the points, as appropriate. In doing so, this discussion should be understood as relying on two-dimensional representations of three-dimensional components as a matter of convenience and example only.

Note that while the cutting tip described above is optimally configured for increased throughput of tissue (i.e., reduced clogging or increased amount of tissue per unit time), this result is achieved not by increasing the dimensions of the device, which would intuitively reduce the chance that a tissue particle of given dimensions would clog the device. Rather, and counter-intuitively, the device has a decreased cutting window, measured with respect to the dimensions of the aspiration path (e.g., tube inner diameter [or ID]), yet achieves reduced clogging.

Another, independent factor which may be employed in some embodiments is to increase the area of the lumen of the first tubular member, which may be accomplished in various ways. For example, neglecting (for simplicity only) the spacing between the first and second tubular members devoted to clearance (and optionally irrigation as described above), and without changing the outer or inner diameters of the second tubular member or the outer diameter of the first tubular member, the inner diameter of the first tubular member may be increased by reducing the thickness of the material of the first tubular member, thus increasing the diameter of the lumen. Or, by keeping such thickness of the first tubular member constant, the outer diameter of the first tubular member (and therefore the inner diameter of the second tubular member) may be increased by reducing the thickness of the second tubular member, and letting the inner diameter of the first tubular member correspondingly increase. Of course, these two approaches could be combined in any proportion subject to the geometrical and materials constraints relevant to the situation. In any event, the cutting window comprises first and second open sections, the first open section of the cutting window having an area denoted A, and the hollow first member having a cross-sectional area denoted B, A and B being in a ratio between about 1:1 and 2:1. This is substantially less than prior devices having a ratio between approximately 3:1 and 4:1, which devices experienced greater rates of clogging than the embodiments disclosed here.

Regardless of how a particular embodiment is described, the surgical cutting instrument and related method of use provides a substantial improvement over previous designs and methods. In particular, optimally configuring the cutting window (i.e., optimizing shape, size, orientation and similar factors in the physical construction of the cutting window) enables a single device to address multiple types of target tissue (soft tissue, thin bone, and the like) with reduced clogging and without requiring the surgeon to change the apparatus during the procedure.

The surgical cutting instrument, and in particular the surgical cutting instrument 30 and other similar designs incorporating a multi-sectional cutting window, as disclosed here, is highly useful for a number of surgical procedures. For example, the surgical cutting instrument can readily be used for an uncinectomy and maxillary sinus antrostomy in which the cutting window is repositioned (without requiring overt movement of the handpiece and/or removal of the cutting implement from the target site) to access the antrostomy superiorly, inferiorly, and posteriorly. Similarly, the surgical cutting instrument of the present invention is well-suited for maxillary polypectomy or removal of fungus, cysts, or other pathology in the maxillary sinus, either through the maxillary antrostomy or through an anterior maxillary trephination. The surgical cutting instrument is also useful with lateral and medial frontal sinusotomy procedures in which the cutting window is applied to cutting laterally, medially, and posteriorly. Other surgical procedures with which the surgical cutting instrument of the present invention is useful include acoustic neuroma, debulking of laryngeal, tracheal, and bronchial lesions, and spinal disc space nucleostomy, to name but a few.

Accordingly, although the invention has been described with reference to preferred embodiments, workers skilled in the art will recognize that changes can be made in form and detail without departing from the spirit and scope of the following claims.

What is claimed is:

1. A surgical cutting instrument for addressing tissue including at least one of soft tissue and bone, the instrument comprising:
    a first hollow elongated member having a proximal section and a distal section having serrated edges which define a cutting tip;
    a second tubular member having a proximal region and a distal region forming a cutting window, the cutting window having serrated edges, the first elongated member being co-axially disposed within the second tubular member such that the cutting tip is exposed at the cutting window; and
    means for moving the first and second members relative to each other around their common axis such that the cutting tip may repeatedly address the tissue;
in which the cutting window comprises a proximal, trapezoidal first open portion having a first width, and a distal, generally semicircular second open portion having a second width, the first and second open portions being separated from each other by a pair of oppositely facing teeth, each of the first and second widths of the open portions being greater than a distance by which each of the pair of oppositely facing teeth are separated from each other.

2. The surgical cutting instrument of claim 1, in which the second width of the distal, generally semicircular second open portion is greater than the first width of the proximal, trapezoidal first open portion.

3. The surgical cutting instrument of claim 1, in which the first portion of the cutting window has an area denoted A, and the hollow first member has a cross-sectional area denoted B, A and B being in a ratio between about 1:1 and 2:1.

4. The surgical cutting instrument of claim 1, further comprising a handpiece.

5. The surgical cutting instrument of claim 1, further comprising an irrigation path connected to the second member.

6. The surgical cutting instrument of claim 1, further comprising an aspiration path connected to the first member.

* * * * *